Figure 1:
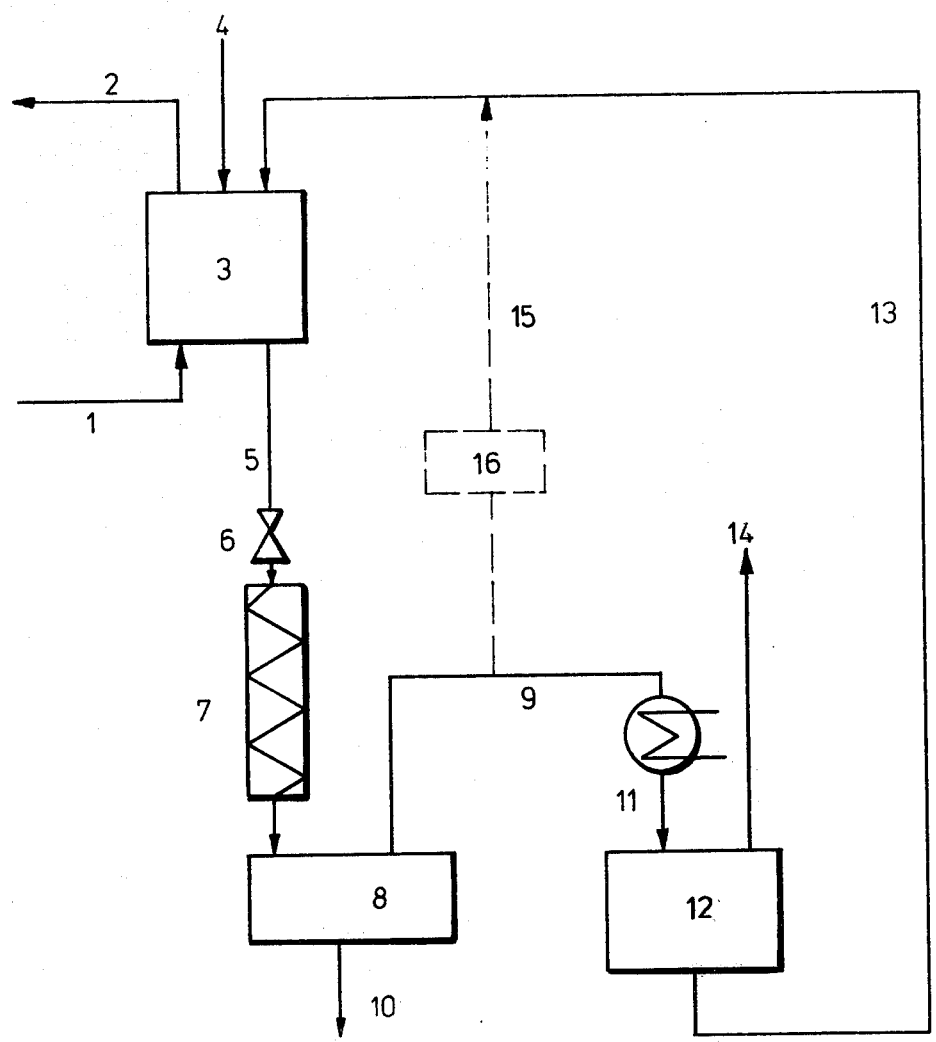

United States Patent

Beilstein et al.

[11] 4,168,283
[45] Sep. 18, 1979

[54] PROCESS FOR DRYING COPPER CONTAINING CATALYST WASTE

[75] Inventors: Günter Beilstein, Dormagen; Clemens Casper, Krefeld; Dieter Grenner, Dormagen; Johannes O. Sajben, Krefeld, all of Fed. Rep. of Germany

[73] Assignee: Bayer Aktiengesellschaft, Leverkusen, Fed. Rep. of Germany

[21] Appl. No.: 947,136

[22] Filed: Sep. 29, 1978

[30] Foreign Application Priority Data

Oct. 7, 1977 [DE] Fed. Rep. of Germany ....... 2745078

[51] Int. Cl.$^2$ ............................................. C07C 21/00
[52] U.S. Cl. ............................. 260/654 S; 260/654 R
[58] Field of Search ............. 260/654 S, 654 R, 652 P

[56] References Cited

U.S. PATENT DOCUMENTS 4,070,405  1/1978  Baatz et al. ...................... 260/654 R Primary Examiner—Herbert Levine
Assistant Examiner—Joseph A. Boska
Attorney, Agent, or Firm—Sprung, Felfe, Horn, Lynch & Kramer

[57] ABSTRACT

Viscous copper-containing catalyst waste is split up into solid particles and gaseous dichlorobutene along a steadily curved flow path, the liquid film flowing along an inner tube wall being driven along by the gas flowing at a higher rate in the core.

3 Claims, 1 Drawing Figure

PROCESS FOR DRYING COPPER CONTAINING CATALYST WASTE

This invention relates to a process for drying the copper-containing catalyst waste which accumulates in the form of a suspension during an isomerisation reaction, with recovery of dichlorobutene.

In the isomerisation of 1,4-dichloro-2-butene to form 3,4-dichloro-1-butene or vice versa, various catalysts based predominantly on complexes of copper with organic complex formers are used for accelerating the adjustment of equilibrium between the two isomers, the newly formed isomer being removed from the reaction mixture, for example by distillation. Examples of the organic complex formers used for this purpose include adipic acid dinitrile, benzonitrile (British Pat. No. 1,260,691), quaternary ammonium compounds (U.S. Pat. No. 3,819,730=German Offenlegungsschrift No. 2,248,668), pyridine (Japanese Pat. No. 8 451/68), benzonitrile (Japanese Patent No. 8 453/68), naphthenates, oleates, and stearates together with substituted ureas (German Offenlegungsschrift No. 2,212,235). The use of non-complexed copper(I)chloride has also been described (German Auslegeschrift No. 1,233,385).

In every case, the isomerisation reaction takes place endothermically at elevated temperatures (50° to 150° C.). It is accompanied by the formation of relatively high boiling secondary products which accumulate in the reaction mixture. This secondary product formation is also mentioned in a number of Patents (German Offenlegungsschrifts Nos. 1,950,971 and 1,802,385; Japanese Pat. No. 420/66, Belgian Pat. Nos. 788,356 and 763,117 and German Auslegeschrift No. 1,220,847), the extent to which it occurs being smaller with short residence times (obtainable for example by optimal catalysts).

Since it has not yet been possible completely to suppress formation of the high boiling secondary products by suitably carrying out the reaction, part of the reaction mixture has to be removed from the circuit in order to avoid a steady increase in the concentration of high boiling secondary products. This part of the reaction mixture has to be destroyed, combustion involving considerable complications when it comes to cleaning of the smoke gases both on account of the evolution of HCl from the dichlorobutene and on account of the formation of copper-containing dust.

According to German Offenlegungsschrift No. 2,532,472, the dissolved copper complex is worked up by precipitation and filtration following the addition of an apolar solvent. This process is attended by the disadvantage of high investment and operating costs.

According to German Offenlegungsschrift No. 1,220,847, the relatively high boiling constituents are distilled off. Working up is complicated, in addition to which pollution problems are encountered during storage of the liquid high-boiling constituents contaminated with copper compounds.

An object of the present invention is to find a process in which the dichlorobutene is recovered as completely as possible and the catalyst waste from copper-containing high-boiling constituents accumulates in a solid phase which shows little tendency towards decomposition and aggression and, hence, lends itself to non-polluting disposal.

According to the invention, this object is achieved by a process in which the suspension having a solids content of from 1 to 15% by weight is let off at a temperature of from 70° to 150° C. into a steadily coiled tube, in which the ratio of tube diameter to radius of curvature is in the range of from 0.01:1 to 0.1:1, at least 15% by weight of the suspension being evaporated, and in which the rest of the suspension is subsequently dried on passing through the tube with a pressure loss of from 100 to 2000 mbars and a simultaneous reduction in temperature to 50°–120° C., in order thereafter to be separated in a separator into solid, particulate catalyst waste and gaseous dichlorobutene.

The advantages afforded by the invention lie in particular in the fact that, in addition to the recovery of dichlorobutene, a solid particulate waste of low moisture content is obtained which, by virtue of its compactness, minimal tendency towards chemical change and the considerable reduction in aggressiveness, can now be stored without any danger of pollution, for example in normal containers or casks.

Accordingly, it was surprising to the expert to find that, during the transition from the liquid to the dry phase, the tar-like state did not result in blockages or at least in local overheating which could have destroyed the tube and/or have led to the formation of an inhomogeneous waste whose storage would have been difficult on account of decomposition of the substance or on account of exothermic polymerisation.

Neither was it foreseeable how a suspension, in which the individual constituents differ considerably in their coefficients of friction, would behave in a vapour stream, particularly during phase transition.

The process according to the invention provides for a short residence time at a temperature which may be determined in advance, so that it may be optimally carried out. The yield is high. The process using a coiled tube is extremely economical because the evaporated dichlorobutene is simultaneously used as a propellant and is finally recovered.

One example of an embodiment of the invention is illustrated in the accompanying drawing and described in detail in the following.

In the drawing, 1,4-dichloro-2-butene is introduced into an isomerisation reactor (3) through a pipe (1). At the same time, a catalyst is introduced through a pipe (4). Some of the 1,4-dichloro-2-butene is converted in an endothermic reaction into 3,4-dichloro-1-butene. The resulting mixture of both isomers is delivered through a pipe (2) to a distillation unit (not shown) for recovering the 3,4-dichlorobutene.

Part of the content of the reactor is run off through a pipe (5), either continuously or at intervals, and sprayed through an expansion valve (6) into a steadily coiled tube (7) in which it is concentrated by evaporation to such an extent that a solid, particulate product accumulates in a following separation chamber (8), whilst the dichlorobutenes are run off in the gas phase through a pipe (9). The solid product is discharged through a pipe (10). It does not undergo any changes during storage and may be disposed of. To this end, it is best packaged in casks or bags of suitable material.

The dichlorobutenes are liquefied in a condenser (11) and collected in a receiver (12) from which they may be pumped back through a pipe (13) into the isomerisation reactor (3). Any entrained solid fractions are only present in negligible quantities, so that recycling does not have any adverse effects upon the function of the isomerisation reactor (3). Finally, the installation is connected through a pipe (14) to a vacuum system (not shown).

In one variant (shown in chain lines), the gaseous dichlorobutene mixture is directly pumped back into the reactor through a pipe (15) and a vacuum station (16) without intermediate condensation.

EXAMPLE

The apparatus of the drawing is used and the percentages are by weight.

In order to maintain the concentration levels of 1.8% of copper chloride in complex form, 8.1% of high-boiling constituents and solids, 12.1% of 3,4-dichloro-1-butene and 78.0% of 1,4-dichloro-2-butene, 120 kg of per hour high-boiling catalyst waste are removed from an isomerisation reactor and delivered to a steadily coiled tube (7) (nominal width 25 mm, radius of curvature 650 cm, length 18 m) at a temperature of 128° C. Concentration by evaporation takes place with a pressure loss of 500 mbars in such a way that a solid residue containing dichlorobutene still bound by adsorption (internal moisture) accumulates in a quantity of 18.7 kg/h. At the outlet end of the coiled tube (7), the temperature amounts to 80° C. and the pressure to 70 mbars.

The vapours running off through (8) and (9) are liquefied in the condenser (11) and collected in the receiver (12). In addition to the dichlorobutenes as its main constituents, the condensate (101.3 kg/h) contains 0.09% of copper chloride and 0.22% of high-boiling fractions and is returned through the pipe (13) to the isomerisation reactor (3). Recycling of the condensate improves the yield of dichlorobutenes by this quantity.

We claim:

1. A process for drying copper-containing catalyst waste which accumulates in the form of a suspension during the isomerisation of 1,4-dichloro-2-butene to 3,4-dichloro-1-butene or vice versa, which comprises introducing the suspension having a solids content of from 1 to 15% by weight at a temperature of from 70° to 150° C. into a steadily coiled tube in which the ratio of tube diameter to radius of curvature is in the range of from 0.01:1 to 0.1:1, evaporating at least 15% by weight of the suspension, subsequently drying the rest of the suspension on passing through the tube with a pressure loss of from 100 to 2000 mbars and a simultaneous reduction in temperature to 50°–120° C., and thereafter separating same in a separator into solid particulate catalyst waste and gaseous dichlorobutene.

2. A process as claimed in claim 1, wherein the gaseous dichlorobutene is directly pumped back from the separator to the isomerisation reactor.

3. A process for isomerising 1,4-dichloro-2-butene to 3,4-dichloro-1-butene or vice versa, in which copper-containing catalyst waste is dried by a process as claimed in claim 1 or 2.

* * * * *